(12) United States Patent
Yang

(10) Patent No.: US 9,990,857 B2
(45) Date of Patent: Jun. 5, 2018

(54) METHOD AND SYSTEM FOR VISUAL PEDOMETRY

(71) Applicant: Grafty, Inc., Sunnyvale, CA (US)

(72) Inventor: Allen Yang Yang, Fremont, CA (US)

(73) Assignee: GRAFTY, INC., Sunnyvale, CA (US)

( * ) Notice: Subject to any disclaimer, the term of this patent is extended or adjusted under 35 U.S.C. 154(b) by 161 days.

(21) Appl. No.: 15/199,573

(22) Filed: Jun. 30, 2016

(65) Prior Publication Data

US 2017/0004631 A1 Jan. 5, 2017

Related U.S. Application Data

(60) Provisional application No. 62/187,688, filed on Jul. 1, 2015.

(51) Int. Cl.
| | |
|---|---|
| *G06K 9/00* | (2006.01) |
| *G09B 5/02* | (2006.01) |
| *G01C 22/00* | (2006.01) |
| *G06F 19/00* | (2018.01) |
| *G06T 7/246* | (2017.01) |
| *A63B 22/00* | (2006.01) |
| *A63B 22/02* | (2006.01) |
| *A63B 22/06* | (2006.01) |
| *A63B 71/06* | (2006.01) |
| *A61B 5/11* | (2006.01) |

(52) U.S. Cl.
CPC ............... *G09B 5/02* (2013.01); *A61B 5/1128* (2013.01); *G01C 22/006* (2013.01); *G06F 19/3481* (2013.01); *G06K 9/00342* (2013.01); *G06T 7/246* (2017.01); *A61B 5/112* (2013.01); *A63B 22/0076* (2013.01); *A63B 22/02* (2013.01); *A63B 22/0605* (2013.01); *A63B 22/0664* (2013.01); *A63B 2071/065* (2013.01); *A63B 2071/0647* (2013.01); *A63B 2071/0658* (2013.01); *A63B 2220/05* (2013.01); *A63B 2220/12* (2013.01); *A63B 2220/17* (2013.01); *A63B 2220/803* (2013.01); *A63B 2220/805* (2013.01); *A63B 2220/806* (2013.01); *A63B 2220/807* (2013.01); *A63B 2220/83* (2013.01); *A63B 2225/20* (2013.01); *A63B 2225/50* (2013.01); *A63B 2244/22* (2013.01); *G06T 2207/30196* (2013.01); *G06T 2207/30241* (2013.01)

(58) Field of Classification Search
None
See application file for complete search history.

(56) References Cited

U.S. PATENT DOCUMENTS

| | | | | |
|---|---|---|---|---|
| 4,337,049 A | * | 6/1982 | Connelly | ........... A63B 24/0003 434/247 |
| 2011/0091073 A1 | * | 4/2011 | Iwasaki | ................... G06T 7/215 382/103 |
| 2013/0090881 A1 | * | 4/2013 | Janardhanan | ........ G01C 22/006 702/104 |
| 2014/0274567 A1 | * | 9/2014 | McCready | ......... A63B 71/0622 482/8 |

* cited by examiner

*Primary Examiner* — Shervin Nakhjavan
(74) *Attorney, Agent, or Firm* — Orrick, Herrington & Sutcliffe LLP

(57) ABSTRACT

A system and method for calculating step count and associated physical movement intensity. In some embodiments, the system includes at least a camera to capture video of user motions, which are analyzed, and the corresponding step count and physical exercise intensity are deduced by the disclosed method.

20 Claims, 6 Drawing Sheets

METHOD AND SYSTEM FOR VISUAL PEDOMETRY

CROSS-REFERENCE TO RELATED APPLICATIONS

This application claims priority to U.S. Provisional Patent Application No. 62/187,688, which was filed Jul. 1, 2015. The disclosure of the Provisional Patent Application is herein incorporated by reference in its entirety and for all purposes.

FIELD

The present disclosure relates to visual pedometry, and more specifically, but not exclusively, to a system and method for capturing video of user motions and determining a corresponding step count and physical exercise intensity.

BACKGROUND

The implementation of a pedometry function is traditionally based on an electronic device called a pedometer. The pedometer counts steps that a user takes by detecting the movement of certain body parts, such as hands and hips. The pedometry output typically is represented numerically by steps per minute.

Conventional pedometer devices must be physically attached to, or worn by, the user to measure the movement of the user.

Similar to the pedometer, a conventional exercise machine (e.g., treadmills, steppers, elliptical machines, exercise bicycles, rowing machines, and so on) may also include an inertial measurement unit (IMU) that is attached to a part of the exercise machine. The IMU measures movement of the part of the exercise machine where it is attached. The movement can be periodic in nature, corresponding to the steps of the user on the exercise machine.

As used herein, IMUs installed on exercise machines are also referred to as pedometers, as long as the functionality of the IMU is to calculate the user step count and movement intensity.

After the movement of either the user, or the exercise machine part, is measured by a pedometer, the measured signal is transmitted to a computer system, whereby corresponding user movement and steps are estimated based on the measured signal.

However, the traditional pedometry approach has certain limitations. First, as discussed, the pedometer must be physically attached to a part of the user or a part of the exercise machine. In many scenarios, users would prefer not to attach any device either on them or on the exercise machines.

Second, the pedometer must be connected to the computer system to calculate the step count and the physical movement intensity. The connection may be established via wireless or wired communication modules on both the pedometer and the computer system. Therefore, the pedometer must be supplied with sufficient power to activate the onboard IMU sensor and the communication module. Furthermore, in the case of wired connection, installation of a cable connecting the device and the computer can be time and labor consuming, and can be a safety risk on rapidly moving exercise machines. In the case of wireless connection, some wireless communication configurations need to be set up in order to establish the wireless connection, which also can be time and labor consuming.

Third, the cost of manufacturing the pedometer hardware and maintaining the working condition of the pedometer adds to the overall cost of the computer system that provides the functionality of calculating step count and movement intensity.

In view of the foregoing, a need exists for an improved system for determining a step count and physical exercise intensity in an effort to overcome the aforementioned obstacles and deficiencies of conventional pedometry systems.

Figure 1:
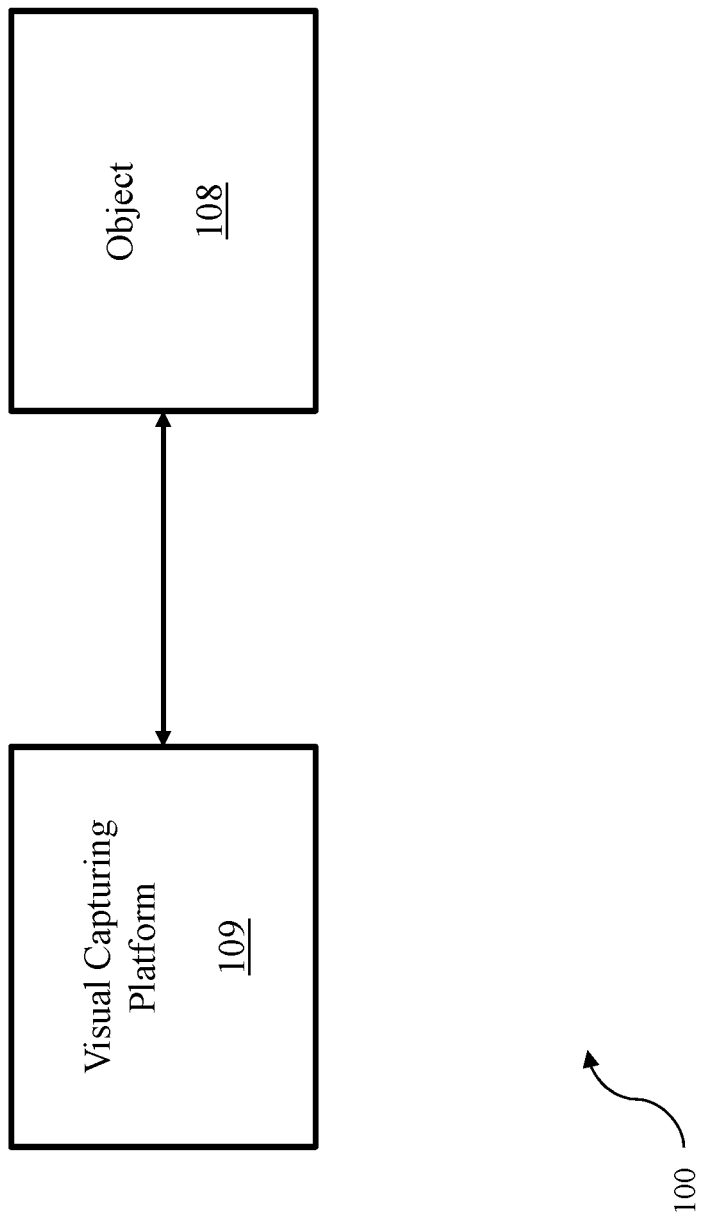
FIG. 1 is an exemplary top-level block diagram illustrating one embodiment of a visual pedometry system.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

Since currently-available pedometry systems are deficient because of power and connectivity limitations, a system for visual pedometry can prove desirable and provide a basis for a wide range of graph computation applications, such as estimating step count and movement intensity. This result can be achieved, according to one embodiment disclosed herein, by a visual pedometry system 100 as illustrated in FIG. 1.

Turning to FIG. 1, the visual pedometry system 100 is shown as including a visual capturing platform 109 for management of an object 108. The visual pedometry system 100 is suitable for use with a wide range of objects 108, such as humans, legged animals, and legged robots. In a preferred embodiment, the object 108 includes a user during an exercise such as shown in FIGS. 2A-B.

In some embodiments, the visual capturing platform 109 includes smart phones, personal digital assistants, cell phones, media players, web cameras, security cameras, drones, and personal computers. In a preferred embodiment, the visual capturing platform 109 is a smart tablet such as an iPad® (manufactured by Apple®) or an Android® (manufactured by Google®) tablet. In other embodiments, the visual capturing platform 109 is a television, such as shown in FIG. 2A.

Figure 2A:
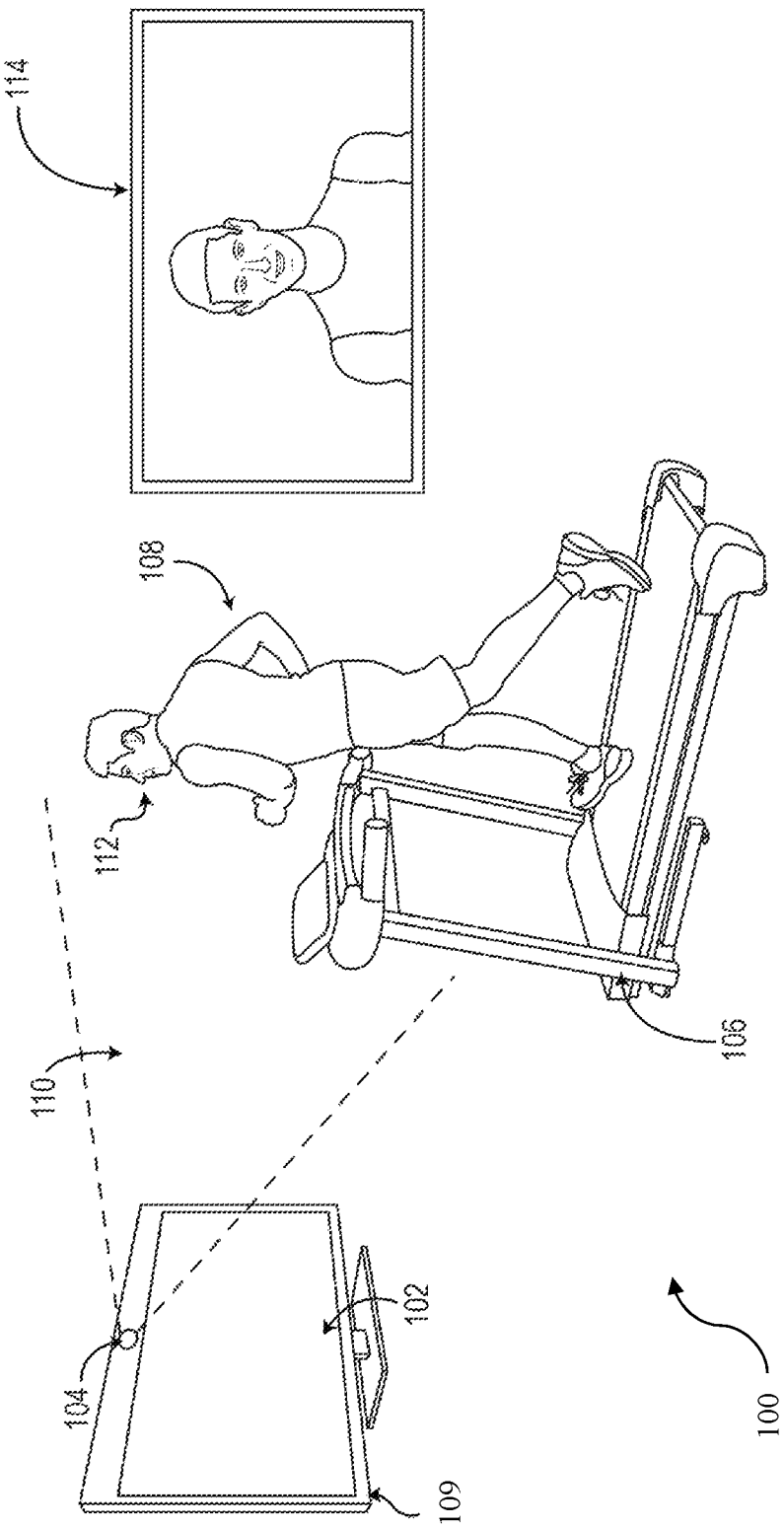
FIG. 2A is an exemplary detailed block diagram illustrating one embodiment of the visual pedometry system of FIG. 1.
Figure 2B:
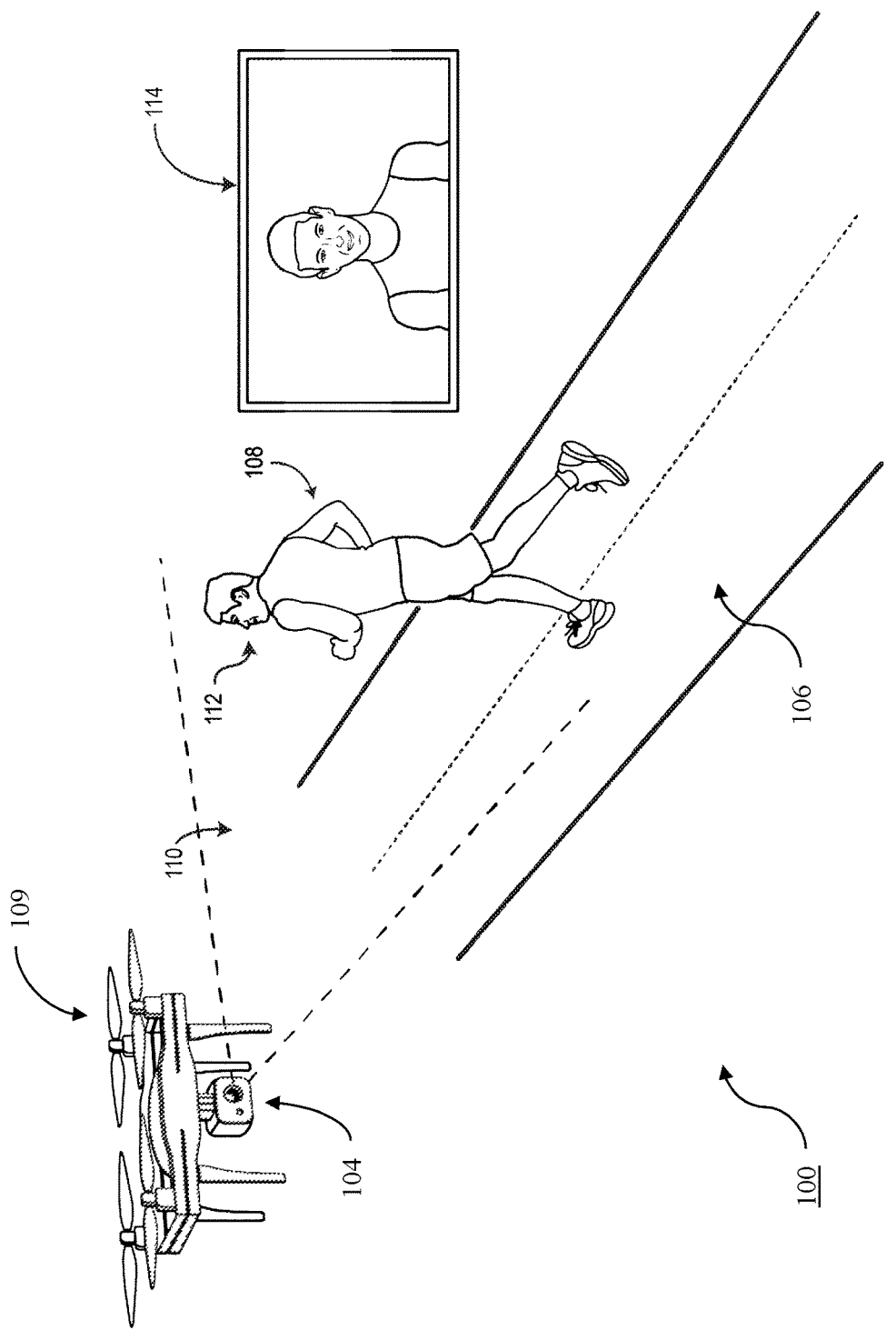
FIG. 2B is an exemplary detailed block diagram illustrating another embodiment of the visual pedometry system of FIG. 1.

With reference to FIG. 2A, the visual capturing platform 109 can be installed at a fixed orientation with respect to the object 108. The visual capturing platform 109 includes an image capturing device 104 that is capable of capturing video of the object 108 while the object 108 is viewing or interacting with the visual capturing platform 109. However, in preferred embodiments, the object 108 does not interact with the visual capturing platform 109. Stated in another way, the user (e.g., object 108) advantageously exercises without any need to alter their performance while the visual capturing platform 109 can receive and process information regarding the exercise.

The image capturing device 104 can include any video camera, infrared sensing camera, still image camera, grayscale and color cameras, camcorders, three-dimensional (3D) cameras (e.g., Microsoft Kinect®, Intel Real Sense®, Sony SoftKinetic® camera, Toshiba® dual-lens depth camera, and Leap Motion camera), and any suitable device that can capture image sequences of the object 108.

The image capturing device 104 is configured to capture a field of view (FOV) 110, where the appearance of objects within the FOV 110 is measured and represented as discrete pixel values in image frames. The output of the image capturing device 104 includes video sequences, each of which contains image frames that are captured consecutively in time according to a frame rate. Although shown as being integrated with the visual capturing platform 109, in some embodiments, the image capturing device 104 can be separate and discrete from the visual capturing platform 109.

In one embodiment where the object 108 performs movement on a platform 106 (e.g., an exercise machine), the orientation of the visual capturing platform 109 and the image capturing device 104 is also fixed with respect to the platform 106. Although not shown, the visual capturing platform 109 and/or the image capturing device 104 can be placed on, or attached to, a frontal panel of the platform 106.

The conventional exercise machine often includes a frontal panel that presents information and a control interface for the object 108. Advantageously, the visual capturing platform 109 and/or the image capturing device 104 can be placed on or attached to the front panel of the exercise machine, while the object 108 remains within the FOV 110.

In another embodiment, the visual capturing platform 109 and/or the image capturing device 104 can be integrated with an exercise machine and become part of the computer module in the exercise machine that includes a camera module capable of capturing video and a computer module capable of executing the disclosed method.

The object 108, or a part of the object 108, that performs movement is within the FOV 110. As shown in FIG. 2A, a frontal face 112 of the user (e.g., object 108) is captured in the FOV 110. An example of an image frame capturing the frontal face 112 is illustrated as an image 114. In some embodiments, when the movement is recorded in consecutive image frames over time, the image capturing device 104 creates a video that captures the representation of the body movement.

The use of a human face and upper body as the content of the image 114 is for illustration purpose only. Examples of the image 114 include other parts of the user's body, such as nose, mouth, eyes, ears, torso, waist, upper extremities, and lower extremities. Other examples include certain apparatus worn by the object 108, such as glasses, wristbands, shoes, gloves, and body markers utilized in motion capturing systems. Other examples further include legged animals, and/or some of their body parts, and/or certain apparatus worn by or attached to the animals. Other examples further include legged robots, and/or some of their body parts, and/or certain apparatus worn by or attached to the robots.

The FOV 110 of the image capturing device 104 is not limited to user video from the frontal position (e.g., the front face 112). For example, the image capturing device 104 can be placed facing the side of the object 108, i.e., the profile view, or the back of the object 108, i.e., the back view.

Figure 3:
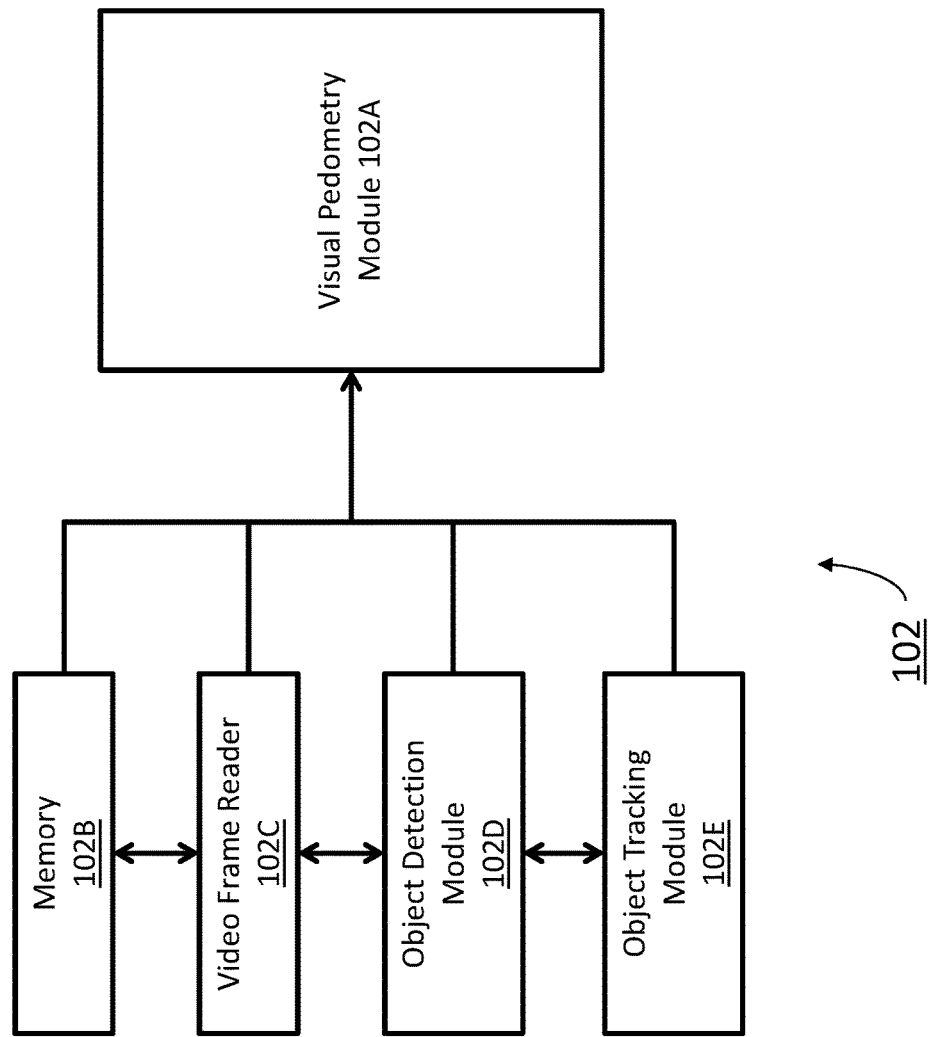
FIG. 3 is an exemplary detailed block diagram illustrating one embodiment of the computer module of FIG. 2A.

The visual capturing platform 109 can include a computer module 102, as illustrated in FIG. 2A. The computer module 102 can include but is not limited to a computer, a processing unit, memory, and so on. The computer module 102 performs any processing of the data received via the image capturing device 104. With reference to FIG. 3, in one embodiment, the computer module 102 includes a memory 102b, a video frame reader 102c, an object detection module 102d, an object tracking module 102e, and a visual pedometry module 102a.

The memory 102b stores data captured by the visual capturing platform 109 and/or the image capturing device 104. For example, the memory 102b can represent a computer file system that maintains and manages video data, one or more image frames, and other multimedia formats. In some embodiments, the memory 102b includes any computer storage, such as random access memory (RAM), read-only memory (ROM), electrically erasable programmable ROM (EEPROM), flash memory, compact discs (CD), digital versatile disks (DVD), optical storage, magnetic cassettes, magnetic tape, magnetic disc storage, and/or any other medium which can be used to store selected information.

The video data, one or more image frames, and other multimedia formats received from the visual capturing platform 109 and/or the image capturing device 104 are processed by the video frame reader 102c. Specifically, the video frame reader 102c receives one or more video frames from a video file and provides individual video frames to the visual pedometry module 102a, the object detection module 102d, and the object tracking module 102e. Each video frame can include an image that is grouped sequentially in the video based on the time they are captured.

Given a selected video frame from the video frame reader 102c, the object detection module 102d detects coordinates of one or more image regions of the selected video frame that might include an image of the object 108. The image regions that include that object 108 are provided to the object tracking module 102e.

The object tracking module 102e can track a specific object region that has been identified by the object detection module 102d. The object tracking module 102e performs a search for an image region in the selected video frame that includes similar image attributes that can be used to describe an image region containing the object from a previous frame.

In some embodiments, the object tracking module 102e can be omitted. In these embodiments, every object region is detected by the object detection module 102d anew, and the tracking information can be ignored between consecutive frames.

The visual pedometry module 102a manages the movements of the image regions that include the object 108 and can analyze/process the corresponding step count from the movements that represent possible steps of the object 108.

Returning to FIG. 2A, the computer module 102 is shown to be integrated with the visual capturing platform 109 for illustrative purposes only. In other embodiments, the visual capturing platform 109 can be physically separate from the computer module 102. More specifically, the computer module 102 can be a standalone computing device that connects to the visual capturing platform 109 remotely via a communication network (not shown).

Furthermore, the computer module 102 can process the video data captured by the visual capturing platform 109 simultaneously and/or at a later time. In one embodiment, the visual capturing platform 109 can first capture the images of the object 108 and save the video data in a file system (not shown). At a later time, the computer module 102 can obtain the video data from the file system into its memory 102B and proceed to estimate the step count of the object 108 recorded in the video file. In another embodiment, the computer module 102 can estimate the step count of the object 108 immediately upon receiving the video data via the visual capturing platform 109.

FIG. 2A illustrates the platform 106 as a conventional treadmill. Other examples of the platform 106 include exercise machines, such as elliptical machines, rowing machines, and stationary bikes, and cardiac stress machines for medical test purposes. Additional examples of the platform 106 include dancing platforms.

In yet another embodiment, the platform 106 can include any outdoor track such as shown in FIG. 2B, and is not limited to any exercise machine. Turning to FIG. 2B, the visual capturing platform 109 and/or the image capturing device 104 also can be installed on an aerial or ground vehicle, such as a quadrotor helicopter or a conveyor belt, with an onboard camera module. The image capturing device 104 communicates with the computer module 102 either directly (e.g., when both the computer module 102 and the image capturing device 104 are disposed onboard the vehicle) or indirectly (e.g., remotely over a wireless communication network (not shown)). The vehicle is capable of adjusting its position and camera orientation in real time to maintain a stable relative distance and camera orientation between the image capturing device 104 and the object 108. In this embodiment, the platform 106 can refer to an indoor or outdoor field where the user performs certain movement, exercise, or game.

Figure 4A:
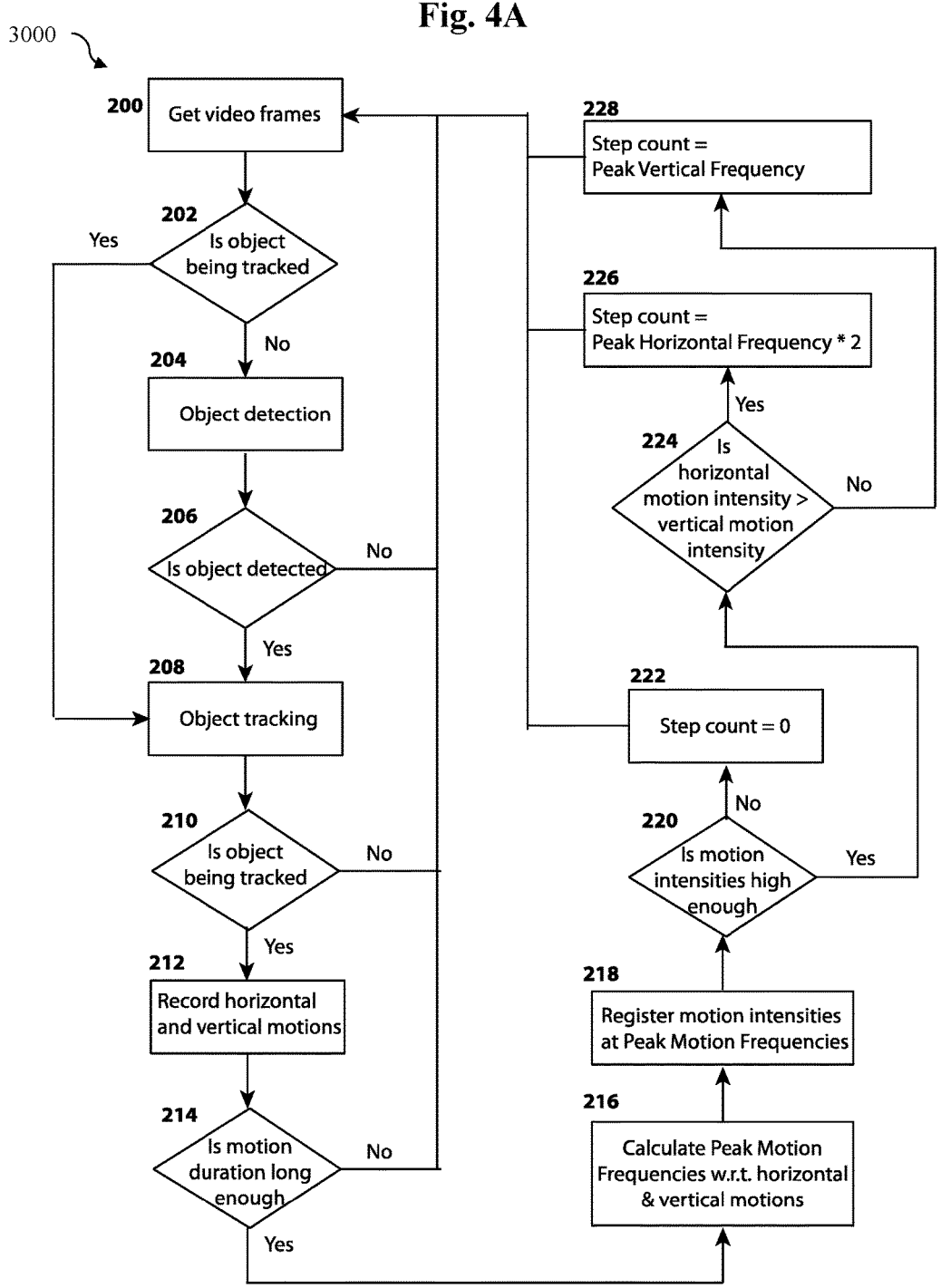
FIG. 4A is an exemplary flow diagram illustrating one embodiment of a visual pedometry method used by the visual pedometry system of FIG. 1.

The visual pedometry system 100 can manage the object 108 in any suitable manner discussed above, including via an exemplary process 3000 for visual pedometry, shown in FIG. 4A. In some embodiments, the process 3000 can be executed via the computer module 102. Turning to FIG. 4A, the process 3000 begins when the video frame reader 102c receives one or more image frames (e.g., video sequence) from the image capturing device 104, at 200.

When a new image frame is received from the image capturing device 104, the object detection module 102d determines whether an object of interest (e.g., the object 108) is already being tracked, at 202. In some embodiments, a selected image frame includes one or more regions that include the object of interest and one or more regions that do not contain the object of interest. If an object of interest is being tracked from the preceding video frame (i.e., the preceding video frame includes any region having the object 108), the process 3000 proceeds to object tracking of the current frame, at 208. If an object of interest is not already being tracked, the process 3000 detects an object 108, at 204.

At 204, the object detection module 102d locates a selected object of interest from a selected image frame. Additionally, the object detection module 102d can maintain object tracking information for the selected object of interest. For example, the object detection module 102d identifies an image appearance of an object of interest, a representation of certain image features from the object of interest, and/or a bounding box coordinates of the object of interest. This information can be stored in the object detection module 102d and/or the memory 102b as desired.

Note that the embodiment described in the process 3000 assumes there is a single object of interest in the FOV 110 (e.g., a single user). However, the determination step 202 can be modified to track multiple objects. For example, the object tracking module 102e can pass along the image regions that contain the tracked object or objects to the visual pedometry module 102a, at 208, and concurrently pass along the rest of the image regions to the object detection module 102d, at 204, to detect new possible objects from the rest of the image regions.

Moving forward, at 204, the object detection module 102d attempts to detect new objects that are not being tracked in the current image frame. The object detection module 102d positively identifies the presence of at least one object of interest in the image frame and identifying the image coordinates of pixels in the image that represent the object of interest.

For example, in some embodiments, the object of interest is the face of a user. In computer vision, methods for detecting human faces are referred to as face detection methods. For example, a face detection method can be implemented using the Viola-Jones method, proposed by P. Viola and M. Jones in an article entitled "Robust Real-Time Object Detection," International Journal of Computer Vision, 2001, which is hereby incorporated by reference in its entirety and for all purposes. At 204, the object detection module 102d detects the image coordinates of the pixels that represent the image of the face of the user (e.g., object 108).

The present disclosure is not limited to detecting faces as objects of interest for object tracking at 208 and for recording the user's horizontal and vertical motions at 212.

In other embodiments, other parts of the user's body can also be treated as objects of interest. Examples include the user's nose, mouth, eyes, ears, torso, waist, upper extremities, and lower extremities. For instance, a method that implements the shoulder detection is known as Histogram of Oriented Gradients, proposed by N. Dalal and B. Triggs in an article entitled "Histograms of Oriented Gradients for Human Detection," at International Conference on Computer Vision and Pattern Recognition, 2005, which is hereby incorporated by reference in its entirety and for all purposes. The object detection module 102d detects the image coordinates of the pixels that represent the image of the shoulders of the user (e.g., object 108), at 204.

In other embodiments, selected apparatus disposed on/worn by the object 108 can be treated as an object of interest as well. Examples include a hat, a pair of glasses, a wristband, shoes, gloves, and body markers utilized in motion capturing systems.

In other embodiments, legged animals and/or some of their body parts can be treated as objects of interest. Furthermore, certain apparatus worn by or attached to the animals also can be treated as objects of interest.

In other embodiments, legged robots and/or some of their body parts can be treated as objects of interest. Furthermore, certain apparatus worn by or attached to the robots also can be treated as objects of interest.

At 206, the object detection module 102d verifies whether at least an object is successfully detected at 204. If not, the process 3000 returns to 200 and retrieve the next video frame. If yes, the object detection module 102d updates the object tracking information at 208.

At 208, the object tracking module 102e updates object tracking information from the preceding video frame to the current video frame. As previously described, the information includes, but is not limited to, the image appearance of an object of interest, the representation of certain image features from the object of interest, and/or the bounding box coordinates of the object of interest.

In step 210, the object tracking module 102E verifies whether the object tracking update performed in step 208 is successful. An unsuccessful condition includes, but is not limited to, a large appearance change about the image of the tracked objects or objects, a predefined percentage of the tracked image features being rejected from the current object image, and/or a bounding box size being too small or too large with respect to the dimensions of the video frame.

In one embodiment, object tracking module 102e updates object tracking based on a robust image features. One type of robust image feature is known as "good features to track," proposed by J. Shi and C. Tomasi. Additional information regarding the "good features to track" is described in an article entitled, "Good Features to Track," 1994 IEEE Conference on Computer Vision and Pattern Recognition (CVPR'94), 1994, pp. 593-600, by J. Shi and C. Tomasi, available at http://www.ri.cmu.edu/publication_view.html-?pub_id=3266, which is hereby incorporated by reference in its entirety and for all purposes. In the robust image tracking feature, once an object image region is detected at 204, a set of robust image features are detected from within the said image region.

Given two adjacent video and/or image frames in time, a sparse or dense optical flow can be computed to establish correspondences between similar robust image features within neighborhoods of the image space. When the optical flow fails to find correspondence for one image feature in the preceding video frame, or the correspondence distance between an image feature in the preceding image frame and its corresponding image feature in the current image frame is larger than an image distance threshold, the image feature in the preceding video frame is said to be rejected from the current video frame. For those image features that have successfully established valid correspondence, they will be registered as the current tracked image features, and they will be used to calculate the optical flow correspondence with the adjacent following frame.

Moving onto step 212, when an object 108 is being tracked, its motion in the image space can be represented by a trajectory over several consecutive video and/or image frames. This information can also be maintained in the memory 102b and/or the object tracking module 102e. The number of consecutive video and/or image frames from which the trajectory is maintained is called the duration of the motion.

Furthermore, a trajectory expressed in the image space can be separated into two perpendicular motions, for example, horizontal motion and vertical motion. The horizontal motion trajectory records the horizontal coordinates of the tracked object image region in the duration of the motion. The vertical motion trajectory records the vertical coordinates of the tracked object image region in the duration of the motion. In visual pedometry, a body movement that is substantially vertical can correspond to one-step over one vertical cycle (e.g., via elliptical machines); whereas a body movement that is substantially horizontal can correspond to two steps over one horizontal cycle (e.g., via treadmills). The process 3000 advantageously identifies both horizontal and vertical movements in order to accurately predict the step counts.

In step 214, the visual pedometry module 102a verifies whether the current duration of the motion trajectories is long enough compared to a predefined video duration threshold. Typically, the video duration threshold is equal to a few seconds in time multiplied by the number of frames per second. For instance, if the intended duration in time is five seconds, and the video is captured at thirty frames per second, then the video duration threshold is equal to one hundred fifty frames.

If the recorded motion duration is not long enough, the video frame reader 102c retrieves the next video frame. Otherwise, the process 3000 proceeds to 216 to estimate the step count and movement intensity using the horizontal and vertical motion trajectories recorded within the current motion duration.

In step 216, the visual pedometry module 102a calculates the frequency responses of the horizontal motion trajectory and the vertical motion trajectory. The calculation can be done by applying a fast Fourier transform (FFT) on each of the said trajectories. Nevertheless, the disclosed method is not limited to using FFT to calculate the frequency response of a time-domain series. Other examples include Discrete Fourier Transform (DFT) and Discrete Cosine Transform (DCT).

In each of the horizontal motion frequency response and the vertical motion frequency response, the visual pedometry module 102a finds its Peak Motion Frequency and registers the frequency response value at the said Peak Motion Frequency at 218. Furthermore, the Peak Motion Frequency corresponding to the horizontal motion trajectory is referred to as Peak Horizontal Frequency, and the Peak Motion Frequency corresponding to the vertical motion trajectory is referred to as Peak Vertical Frequency.

More specifically, the Peak Motion Frequency is detected within a range of discrete frequencies. The range can be defined to be the full frequency range of the FFT transform. Alternatively, in one embodiment, since the range of step count that a human user can achieve is typically limited, the range of the Peak Motion Frequency can be limited to a reasonable range of achievable frequencies. For example, one can reasonable assume the highest possible step count is 300 steps per minute, which corresponds to 300/60=5 Hz, as the highest possible frequency.

To identify the Peak Motion Frequency, in one embodiment, the visual pedometry module 102a traverses the range of the discrete frequencies from the highest frequency to the lowest. The first frequency—whereby its corresponding frequency response value constitutes a local peak value—is set as the Peak Motion Frequency.

The Peak Motion Frequency may be identified by other methods. In another embodiment, a search method traverses the range of the discrete frequencies from the lowest frequency to the highest. The first frequency that includes a corresponding frequency response value with a local peak value is set as the Peak Motion Frequency.

In another embodiment, the Peak Motion Frequency is identified as the one that corresponds to the greatest frequency response value within the lowest frequency and the highest frequency range.

In another embodiment, the Peak Motion Frequency is identified directly from the time series of the horizontal or vertical motion trajectories, without the need to perform a frequency transform. This embodiment counts the frequency of local maximal and/or local minimal points, also called extremal points, in a motion trajectory within the duration of the motion. The Peak Motion Frequency is set to be the frequency of the local maximal points.

Subsequently, the frequency response value at the Peak Motion Frequency is designated as the motion intensity for either the horizontal motion or the vertical motion, respectively.

In one embodiment, whereby there is no frequency response value for either the horizontal motion or the vertical motion that satisfies the conditions for Peak Motion Frequency, the corresponding horizontal motion intensity and vertical motion intensity are set to zero.

In step 220, the visual pedometry module 102a tests if either of the horizontal motion intensity and vertical motion intensity is sufficiently high. For example, the test can be implemented by comparing the said intensity values with a pre-set intensity threshold.

In one embodiment, when neither the vertical motion nor the horizontal motion includes or represents a step motion relevant to the object, none of their corresponding Peak Motion Frequency intensities will be high enough. Hence, the step count is set to zero at 222, and subsequently the process proceeds to retrieve the next video frame at 200.

If at least one of the horizontal motion intensity and vertical motion intensity is higher than the pre-set intensity threshold, the process moves on to step 224.

In step 224, the visual pedometry module 102a tests whether the value of the horizontal motion intensity is greater than the value of the vertical motion intensity. If the test is negative, the visual pedometry module 102a sets the step count to be equal to the Peak Vertical Frequency in 228.

If the test at 224 is positive, the visual pedometry module 102a sets the step count to be equal to twice the Peak Horizontal Frequency at 226. For example, one cycle of a horizontal motion corresponds to two steps.

The value of the step count at 226 or 228 can be further converted from Hz to steps per minute.

In other embodiments of the process 3000, variations in the step 224, step 226, and step 228 can be considered.

For example, the step count can be set to be equal to the Peak Vertical Frequency, regardless of the horizontal motion. The step count can be also set to be equal to twice the Peak Horizontal Frequency, regardless of the vertical motion. The step count can be also set to be the average of the Peak Vertical Frequency and twice the Peak Horizontal Frequency. The step count can be also set to be a moving average over time of the Peak Vertical Frequency and/or twice the Peak Horizontal Frequency within a pre-set duration of the motion. The step count can be further set to be the output of a filtering function that tracks and predicts the optimal step count estimate, given the present and/or the past Peak Vertical Frequencies and Peak Horizontal Frequencies. One instance of such filtering functions is Kalman filtering.

Figure 4B:
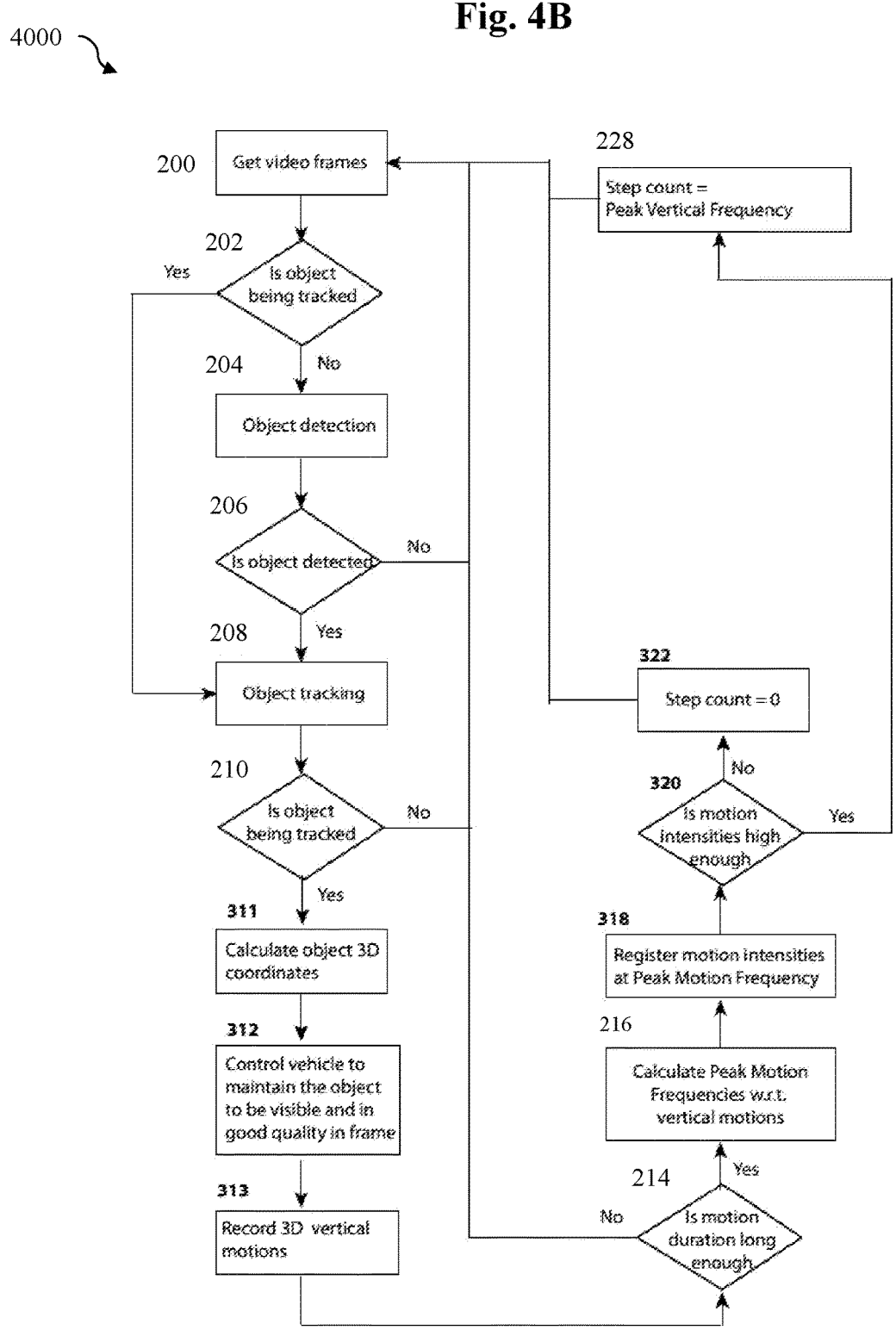
FIG. 4B is an exemplary flow diagram illustrating another embodiment of the visual pedometry method that can be used with the visual pedometry system of FIG. 2B.

Therefore, the process 3000 advantageously estimates step counts based on the at least one visual capturing platform 109. Even further, the process 3000 is particularly suited for stationary embodiments, such as those shown in FIG. 2A, but can also be applied to non-stationary cases, such as shown in FIG. 2B. For example, as shown in FIG. 2B, the visual capturing platform 109 can be located on a moving vehicle that moves with respect to the object 108. Turning to FIG. 4B, a process 4000 for visual pedometry is illustrated for the non-stationary embodiment of FIG. 2B.

Similar to process 3000, the process 4000 begins when video frames are received from the image capturing device 104 at 200. After determining that an object is being tracked, the object tracking module 102e verifies whether the object tracking update performed in step 208 is successful.

If so, the object tracking module 102e calculates the 3-dimensional (3D) coordinates (x, y, z) of the tracked object, at 311. In some embodiments, the 3D coordinates are established by concatenating the 3D coordinates of the visual capturing platform 109 (x0, y0, z0) and the relative 3D coordinates from the visual capturing platform 109 to the object 108 (x1, y1, z1). In other words, (x, y, z)=(x0, y0, z0)+(x1, y1, z1).

For instance, if the visual capturing platform 109 is stationary, then its own 3D coordinates can be assumed to be at the origin (x0=0, y0=0, z0=0). Therefore, the relative 3D coordinates (x1, y1, z1) from the visual capturing platform 109 to the object 108 are the 3D coordinates of the object 108. However, the assumption of the origin (0, 0, 0) as the 3D coordinates of the visual capturing platform 109 is only for convenience and for illustration purposes. Any other 3D coordinates can be used.

In other cases, if the visual capturing platform 109 is non-stationary, its 3D coordinates at the beginning of the process 4000 at time t=0 can be assumed to be at the origin (0, 0, 0). As the visual capturing platform 109 moves, the computer module 102 first updates 3D coordinates of the visual capturing platform 109 at time t as (x0, y0, z0). For instance, the computer module 102 on an aerial vehicle can calculate (x0, y0, z0) by referencing the Global Positioning System (GPS). On a ground wheeled vehicle, the calculation of (x0, y0, z0) can also be done by recording the vehicle's wheel movement. On a conveyor belt, the calculation of (x0, y0, z0) can be done by referencing the location of the camera module 104 on the conveyor belt.

The object tracking module 102e then calculates the relative coordinates between the visual capturing platform 109 and the object 108. For instance, if the camera module 104 on the visual capturing platform 109 is a depth camera, the camera module 104 is capable of directly outputting the relative 3D coordinates (x1, y1, z1). If the camera module 104 is a grayscale camera or a color camera, a method to calculate the relative 3D coordinates (x1, y1, z1) from the camera module 104 to the object 108 is known as structure-from-motion techniques in computer vision. Such techniques are widely available in the literature, such as in the book "An Invitation to 3-D Vision: From Images to Geometric Models" by Yi Ma, Stefano Soatto, Jana Kosecka, and S. Shankar Sastry, which is herein incorporated by reference in its entirety and for all purposes.

The above order of calculating the 3D coordinates of the vehicle (x0, y0, z0) and the 3D coordinates of the object 108 (x1, y1, z1) is for illustration purposes. The order can be reversed, or the calculations can be executed in parallel without an ordering.

In the non-stationary visual capturing platform 109 case, the movement of the visual capturing platform 109 is controlled by the computer module 102. The main objective of the visual capturing platform 109 movement is to maintain the object 108 to be visible within the field of view 110 of the camera module 104. Furthermore, the image of the object 108 in the image 114 should be in good quality. In other words, if the image 114 of the object 108 is too small, the visual capturing platform 109 can move closer to the object 108. Conversely, if the image 114 of the object 108 is too large, the visual capturing platform 109 can move farther away from the object 108.

At 313, the visual pedometry module 102a records the vertical motions of the object, expressed in its z-coordinate, in the memory 102b. In other words, the trajectory of the object is determined in at least three axis: horizontal motion (x-axis), vertical motion (y-axis), and depth motion (z-axis).

The visual pedometry module 102a registers the frequency response value at the the Peak Motion Frequency at 318.

At 320, the visual pedometry module 102a tests if the vertical motion intensity is sufficiently high. For example, the test can be implemented by comparing the intensity values with a pre-set intensity threshold.

In one embodiment, when the vertical motion does not include a step motion, its Peak Motion Frequency intensity will not be high enough. Hence, the step count is set to zero at 322, and subsequently the process 4000 proceeds to retrieve the next video frame at 200.

If the vertical motion intensity is higher than the pre-set intensity threshold, the process 4000 moves on to step 228.

In step 228, the step count is set to be equal to the Peak Vertical Frequency.

The disclosed embodiments are susceptible to various modifications and alternative forms, and specific examples thereof have been shown by way of example in the drawings and are herein described in detail. It should be understood, however, that the disclosed embodiments are not to be limited to the particular forms or methods disclosed, but to the contrary, the disclosed embodiments are to cover all modifications, equivalents, and alternatives.

What is claimed is:

1. A method for measuring step count and movement intensity of an object based on visual pedometry, comprising:
   receiving one or more image frames from an image capturing device;
   selecting the received image frames that include at least a portion of the object;
   determining a trajectory of the object in image space from the selected image frames, wherein the determined trajectory includes at least a horizontal motion or a vertical motion;
   determining a peak horizontal frequency for the horizontal motion trajectory;
   determining a peak vertical frequency for the vertical motion trajectory; and
   setting the step count based on the peak vertical frequency and the peak horizontal frequency.

2. The method of claim 1, wherein said selecting the received image frames further includes maintaining object tracking information of the object for each received image frame.

3. The method of claim 2, wherein said maintaining object tracking information comprises identifying an image appearance of the object, a representation of selected image features being tracked, or a bounding box coordinate of the object.

4. The method of claim 2, wherein said maintaining object tracking information is based on robust image features.

5. The method of claim 1, wherein said determining the peak horizontal frequency includes applying a spatial to frequency domain transform on the horizontal motion trajectory and said determining the peak vertical frequency includes applying a spatial to frequency domain transform on the vertical motion trajectory.

6. The method of claim 1, wherein said determining the peak horizontal frequency is based on a frequency of local extremal points of the horizontal motion trajectory and said determining the peak vertical frequency is based on a frequency of local extremal points of the vertical motion trajectory.

7. The method of claim 1, wherein said image frames are sequentially ordered to represent a video of the object such that a selected image frame has a preceding image frame in the sequence, and said selecting the received image frames includes determining whether the preceding image frame of the selected image frame includes at least a portion of the object.

8. The method of claim 1, wherein said setting the step count based on the peak vertical frequency and the peak horizontal frequency includes setting the step count to be equal to twice the peak horizontal frequency or to be equal to the peak vertical frequency.

9. The method of claim 1, wherein said receiving one or more image frames are received from a non-stationary image capturing device.

10. The method of claim 9, further comprising determining three-dimensional coordinates of the object relative to the image capturing device, and
    determining a trajectory in three-dimensional space, wherein the determined trajectory is based on the determined three-dimensional coordinates.

11. A method for measuring step count and movement intensity of an object based on visual pedometry, comprising:
    receiving one or more image frames from an image capturing device;
    selecting the received image frames that include at least a portion of the object;
    determining three-dimensional coordinates of the object relative to the image capturing device;
    determining a trajectory of the object in three-dimensional space from the selected image frames, wherein the determined trajectory is based on the determined three-dimensional coordinates and includes at least a horizontal motion, a vertical motion, or a depth motion;
    determining a peak vertical frequency for the vertical motion trajectory; and
    setting the step count based on the peak vertical frequency.

12. The method of claim 11, wherein said selecting the received image frames further includes maintaining object tracking information of the object for each received image frame.

13. The method of claim 12, wherein said maintaining object tracking information comprises identifying an image appearance of the object, a representation of selected image features of the object, robust image features, or a bounding box coordinate of the object.

14. The method of claim 11, wherein said determining the peak vertical frequency includes applying a spatial to frequency domain transform on the vertical motion trajectory.

15. The method of claim 11, wherein said determining the peak vertical frequency is based on a frequency of local extremal points of the vertical motion trajectory.

16. A system for measuring step count and movement intensity of an object based on visual pedometry, comprising:
    an image capturing device for capturing one or more image frames;
    an object detection system for selecting the captured image frames that include at least a portion of the object;
    an object tracking system for determining a trajectory of the object in image space or three-dimensional space from the selected image frames, wherein the determined trajectory includes at least a horizontal motion or a vertical motion; and
    a visual pedometry system for determining a peak horizontal frequency for the horizontal motion trajectory, determining a peak vertical frequency for the vertical motion trajectory, and setting the step count based on the peak vertical frequency and the peak horizontal frequency.

17. The system of claim 16, wherein said object tracking system further maintains object tracking information of the object for each captured image frame.

18. The system of claim 16, wherein said image capturing device is a stationary camera relative to the object.

19. The system of claim 16, wherein said image capturing device is a non-stationary camera.

20. The system of claim 19, wherein said visual pedometry system further determines three-dimensional coordinates of the object relative to the image capturing device, and the trajectory in three-dimensional space is based on the determined three-dimensional coordinates and further includes a depth motion.

\* \* \* \* \*